United States Patent [19]

Blondin et al.

[11] Patent Number: 4,808,517

[45] Date of Patent: Feb. 28, 1989

[54] BIOASSAY FOR TOXIC SUBSTANCES

[75] Inventors: George A. Blondin; John M. Harkin, both of Madison, Wis.

[73] Assignee: Wisconsin Alumni Research Foundation, Madison, Wis.

[21] Appl. No.: 813,686

[22] Filed: Dec. 27, 1985

[51] Int. Cl.[4] .................. C12Q 1/00; C12Q 1/48; C12Q 1/34; C12Q 1/26; C12Q 1/32

[52] U.S. Cl. .......................... 435/4; 435/15; 435/18; 435/25; 435/26; 435/810

[58] Field of Search .............. 435/4, 31, 183, 820, 435/810, 18, 26, 25, 15; 436/805, 904

[56] References Cited

PUBLICATIONS

Blondin et al., Archives Biochem. Biophys., 132:509–523 (1969).
Jolly et al., Archives Biochem. Biophys., 130: 191–211 (1969).
Crane et al., Biochem. Biophys. Acta, 22: 475–487 (1956).
Hatefi et al., Biochem. Biophys. Acta, 27: 83–88 (1958).
Hansen et al., Biochem. Biophys. Acta, 81: 214–222 (1964).
Lenag et al., J. Biol. Chem., 241: 5260–5265 (1966).
Beckman Instruments, "Microtox Model 2055 Toxicity Analyzer System."
Bitton, "Bacterial and Biochemical Tests for Assessing Chemical Toxicity in the Aquatic Environment: A Review," Critical Reviews in Environ. Control, 13:1, pp. 51–52 (1984).
Ogata et al., "Classification of Potentially Toxic Chemicals based on Their Effects on Mitochondrial Respiration," Phys. Chem. and Phys. and Med. NMR, 15, pp. 229–232 (1983).

Primary Examiner—Esther M. Kepplinger
Attorney, Agent, or Firm—Lathrop & Clark

[57] ABSTRACT

An assay method is disclosed to test for the presence of toxic substances in environmental samples. The assay uses a suspension of mitochondrial membranes carrying enzymes which can be driven by reverse electron transfer to reduce NAD+ to NADH. The competency of the mitochondrial membrane to accomplish this reduction in the presence of the environmental sample is measured spectrophotometrically to test for toxicants.

27 Claims, 1 Drawing Sheet

BIOASSAY FOR TOXIC SUBSTANCES

BACKGROUND OF THE INVENTION

In recent years it has been widely recognized that the environment has been contaminated with toxic substances, or toxicants, of natural and industrial origins which can, even in trace amounts, cause toxic effects on humans, domesticated animals, and fish and wildlife. Such toxicants can be present in trace amounts in air, soil, water, or foods and foodstuffs and can produce acute or chronic adverse somatic effects in humans or animals exposed to or ingesting these materials, as well as mutagenic, teratogenic or carcinogenic effects. It has therefore become a requirement of our society that environmental sources of substances essential to life, such as surface or ground water used as sources of drinking water, must be examined for trace amounts of an array of toxic substances such as heavy metals, chlorinated pesticides, and volatile organic industrial chemicals, which are very difficult to detect, yet which even in trace amounts may exert deleterious affects on humans or domesticated animals consuming the water. Similar concerns also apply to the protection of fish and wildlife which live in or near lakes and streams which have been inadvertently polluted by man with similar toxicants resulting from human industry. Some of the toxicants, even though present at very low levels in aquatic water systems, are concentrated by biological activity, such as occurs with some chlorinated pesticides and polychlorinated biphenyls and other similar compounds, to thus cause deleterious affects on higher life forms, including both wildlife and humans which consume fish from contaminated waters.

It is therefore useful to have assays which can detect the presence of toxic substances in environmental samples at very low levels. Ideally, it would be beneficial if such assays could be qualitative as well as quantitative by indicating the type of chemical substance which is detected if a positive result is obtained from the assay. However, both qualitative and accurate guantitative chemical analyses of an unknown sample of toxicant are at present very slow and expensive processes. Mixtures present special difficulties because of the need to conduct separate analyses for the constituents thereof. Sometimes even the appropriate analytical methodology and/or toxicological information is not available for individual compounds, particularly new ones. The situation can be even further complicated when multiple toxicants are present in single environmental samples since the interaction between the toxicants can result in additive, synergistic or antagonistic interaction with results that are difficult to predict. Nevertheless, even if qualitative analysis of samples is impractical, sensitive quantitative analysis of samples to screen for the presence of deleterious, even if unknown, toxicants is of great use in determining the safety or the level of contamination of environmental areas. To provide effective tools in risk assessment and to attempt to cope with the problems of rapid assessment of the toxicity of environmental resources, scientists and regulatory officials have sought for some time to develop suitable bioassays for use in quickly screening or examining environmental samples which can be both economical and sensitive. Bioassys typically measure the response of a biological preparation or whole organism to toxic challenges from a sample of unknown constituents, without the need for identifying or quantifying the chemicals concerned, other than quantitatively measuring their effect on biological activity. It has been found that data from such bioassay tests correlate well with affects on laboratory animals and humans when determined by conventional toxicological or epidemiological data. Some prior bioassays have been developed which are based on relatively simple biochemical tests, such as those based on single enzymes or groups of enzymes. Another type of prior bioassay is one based on the responses of whole organisms. One example of a test based on a whole organism approach is the well-known Ames tests for mutagenicity which tests the effect of a sample of known or unknown character on the rate of mutagenic effect on a bacterial strain of known genetic character. Typical bioassays to test unknown environmental toxicants have been done with whole higher organisms such as *Cereodaphnia magna*, water fleas, or selected fish species, such as minnows or rainbow trout, which are sensitive to toxicological effects. One previously known bioassay using whole organisms, in this case bacteria, is based on the light output of the bioluminescent bacterium *Photobacterium phosphoreum* and is marketed by Beckman Instruments under the trade name Microtox. The Mictrotox test utilizes the bioluminescent bacteria, and measures their sensitivity to toxic substances, by noting the quenching of the bioluminescence as the bacteria are adversely affected by dosages of the toxicant.

There is still a need for efficient and economical assays. There is feeling that simple in vitro tests, as for example those using enzymes, are too far removed from whole organisms to qualify as good surrogates, since they are often not sensitive enough to a wide spectrum of toxic agents. On the other end, whole organism tests are often time-consuming and expensive. There are additional problems with whole organism tests, particularly those dependent on microorganisms, in that mutations may cause biological variability in the microorganisms which can cause the results to vary, and in that bacterial cell walls may inhibit the uptake of toxicants, producing falsely negative results in tests.

SUMMARY OF THE INVENTION

The present invention is summarized in that a method of assaying for the presence of toxicants in a sample includes the steps of preparing a suspension of mitochondrial particles formed from the inner membranes of mitochondria; adding substrates to the suspension which are normally metabolized by the oxidative phosphorylating enzymes carried on the particles; adding a quantity of the sample to the suspension; and assaying for the reaction products of the substrates to determine the efficacy of the enzymes on the particles in the presence of the sample.

It is an object of the present invention to provide a method of assaying for the presence of toxic substances in environmental samples which is economical and efficient yet which is based on a sensitive biological system so that the effects of toxic substances on whole biological systems can be modeled.

It is another object of the present invention to provide a kit for use in assaying for the presence of toxic substances in environmental samples which includes suitable substrates and materials so that assays for such toxicants can be quickly and easily performed.

Other objects, advantages, and features of the present invention will become apparent from the following specification.

BRIEF DESCRIPTION OF DRAWING FIGURE

DESCRIPTION OF THE PREFERRED EMBODIMENT

Figure 1:
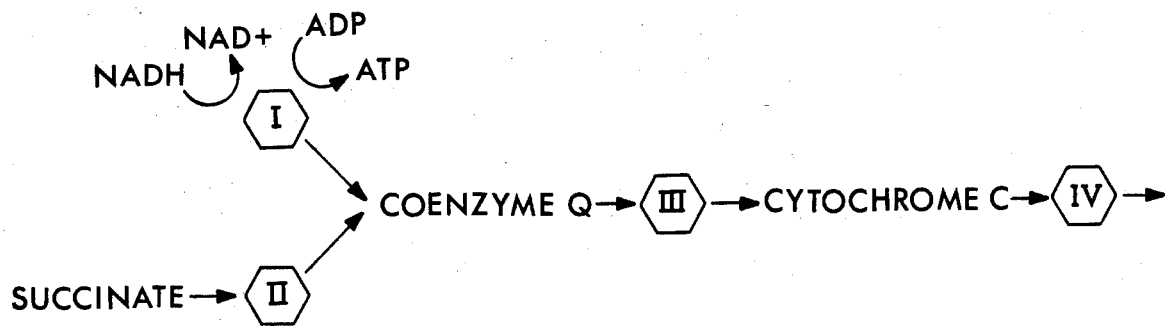
FIG. 1 illustrates in schematic fashion the normal flow of reaction products through the enzyme complexes of the mitochondrial oxidative phosphorylation system.

The method and kit of the present invention make use of mitochondrial preparations as biological assay tools in bioassays intended to detect the presence of toxicants in environmental samples. Mitochondrial preparations present an attractive compromise between the over simplification of most in vitro assays and the time-consuming and expensive nature of sophisticated whole-organism tests. As will be seen below, mitochondrial tests have a high sensitivity, while they are, at the same time, responsive to a broad spectrum of toxic substances.

Mitochondria are cellular organelles which are often characterized as being the biochemical power plant of eukaryotic cells, because mitochondria house the basic biochemical enzymes required to oxidize nutrients on a cellular level to produce energy, largely stored in adenosine triphosphate (ATP), the major energy-storing molecules in cells. In addition, mitochondria perform a variety of other functions involving metabolic and ion-transfer activities which require a highly organized system of enzymes and membrane structures. Most of the enzymes of critical interest, including those in the oxidative phosphorylation chain are carried on the inner membrane of mitochondria and their function is dependent on the competency of that inner membrane and the gradients created across it. The inner membrane is intrinsically impermeable to most ions and most uncharged molecules, so the membrane contains certain specific protein carriers in to transport essential molecules and reaction products and out of the inner membrane space and to maintain proper gradients. The intricacy of the enzymes of mitochondria and their interactions, plus their need for competent membranes, makes the mitochondrial systems highly susceptible to a wide spectrum of toxic substances. Interference with only a single enzyme in a cascade or metabolic chain, or interference with membrane mechanical stability or a membrane transport activity, can upset the fine tuning and disrupt the function of the entire system. It is for this reason that mitochondria make an attractive choice of a subcellular system for use in a bioassay, because they respond with high sensitivity to many toxic compounds present in environmental sample which may operate in diverse ways upon whole biological systems.

The present invention is directed toward the use of a mitochondrial preparation to test for the presence of a toxicant of unknown character in an environmental sample by assaying for the effect of the unknown sample on at least a portion of the oxidative phosphorylation enzyme cascade carried on a mitochondrial membrane. Therefore, to practice the present invention, it is necessary to have a mitochondrial preparation that includes a competent mitochondrial inner membrane carrying thereon the appropriate enzymes. The source of the mitochondrial or submitochondrial particles used in this test is not critical. Conventional mitochondrial preparations such as rabbit heart, rat liver, rat kidney, rat brown fat, or unfractionated beef heart mitochondria, may be used and whole or partial preparations of any such mitochondria are usable within the present process. The preferred mitochondrial preparation for use in the present invention is, however, submitochondrial particles. These submitochondrial particles are bilayer lipid vesicles resulting from micelle formation from the fragments of cristae membranes when whole mitochondria are ruptured. In essence, whole mitochondria from any of the above sources are ruptured by sonication or detergents such as digitonin or treatment in a French press, separated from cytosolic residues by centrifugation, and the membrane segments are then allowed to reform into vesicles which model the behavior of the intact inner membrane of mitochondria. Such submitochondria particles have the asset, in addition to modeling mitochondria behavior, that they may be prepared and frozen or freeze-dried for storage in quantity, so that aliquots of the submitochondrial preparation can be readily available for use in conducting toxicant assays over a long period of time.

To utilize such a mitochondrial preparation as a bioassay for toxicants, it is necessary to calibrate the system measuring the responsiveess of the mitochondrial particles to insult by toxic substances. Accordingly, it is necessary to measure the production or depletion of an enzyme product or substrate over a period of time to determine the effect on the enzyme cascade caused by the environmental sample to which the particles are exposed. It is possible to measure directly respiration rate by measuring oxygen depletion, or creation of ATP, or by measuring ion-specific electrode responses, but such measurements at present require sophisticated instrumentation and technique. It is preferred, for the purposes of the present invention, that a submitochondrial particle is utilized, and that the sensitivity of the response of the enzyme systems on the particle be measured in as simple a method as possible. One simple method is the spectrophotometric analysis of the sample for the presence of NADH. The submitochondrial particles can be caused to engage in reversed electron transfer so as to convert nicotinamide adenine dinucleotide (NAD+) into the reduced form of NADH. The presence of NADH produced from NAD+ can be measured spectrophotometrically by taking advantage of the fact that NADH, and not NAD+, exhibits a light absorptiopn at 340 nanometers. Responses of light adsorption can be quantified by reference to calibrated dose-response curves prepared for appropriate environmental pollutants or mixtures of interest.

The preparation of submitochondrial particles for use in the practice of the present invention therefore begins with the preparation of whole mitochondria. Whole mitochondria from any available source can be used by any known technique capable of reliably separating mitochondria. Beef-heart mitochondria are relatively easy to prepare by the method described by Crane, et al. in Biochem. Biophys. Acta 22:475-487 (1956) or by the method described by Blondin and Green in Arch. Biochem. Biophys. 132:509-523 (1969). The heavy fraction of mitochondria isolated by the procedure described by Hatefi and Lester in Biochem. Biophys. Acta 27:83-85 (1958) gives a more standard preparation which has longer viability. The submitochondrial particles themselves can be prepared from either fresh or frozen mitochondria preferably by the method described by Hansen and Smith in Biochem. Biophys. Acta 81:214-222 (1964). Such submitochondrial particles once prepared can be stored or shipped frozen at −20° C. in a preserving mixture such as that described by Lenaz and MacLennan in J. Biol. Chem., 241:5260-5265 (1966). Alternatively, for storage and shipment the submitochondrial particles can be freeze-dried via the procedure described by Jolly, et al. in Arch. Biochem. Biophys. 130:191-211 (1969). The frozen preparations prepared by this process can simply be thawed to be ready for use in the practice of the present invention. The freeze-dried preparations can be simply reconstituted by wetting with the assay medium shortly before use.

To better understand the method of action of the reverse electron transport phenomenon utilized in the preferred embodiment of the present invention, it is necessary to consider the five different enzyme complexes conventionally recognized in the oxidative phosphorylation chain in mitochondria. As can be viewed in FIG. 1, enzyme complex I catalyzes the reduction of NADH to NAD+ at the same time that ADP is converted to ATP in the reaction. Electron flow is from the enzyme complex I toward coenzyme Q and from thereafter to enzyme complex III. Meanwhile, succinate is oxidized in enzyme complex II to produce an alternative source of electron flow into the system. From coenzyme Q, the electron flow proceeds through enzyme complex III to cytochrome c to enzyme complex IV, which ultimately transfers electrons to molecular oxygen. Each of the enzyme complexes in the oxidative phosphorylation chain can be inhibited selectively by individual toxicants. For example, complex I can be inhibited by rotenone, complex II by thenoyltrifluoroacetone, complex III by antimycin, complex IV by cyanide, and complex V by oligomycin. It is particularly the inhibitory affect of antimycin on enzyme complex III which is of use in the practice of the present invention. Each of the enzyme complexes consists of a series of enzymes embedded in the inner mitochondrial membrane and linked together for efficient interaction. Thus, in addition to being subject to specific inhibition, each complex depends on the competency of the membrane for successful operation. The membrane contains other enzymes, such as ATPase, also essential to oxidative phosphorylation, or reverse eletron transfer, which must operate for the system to function.

Figure 2:
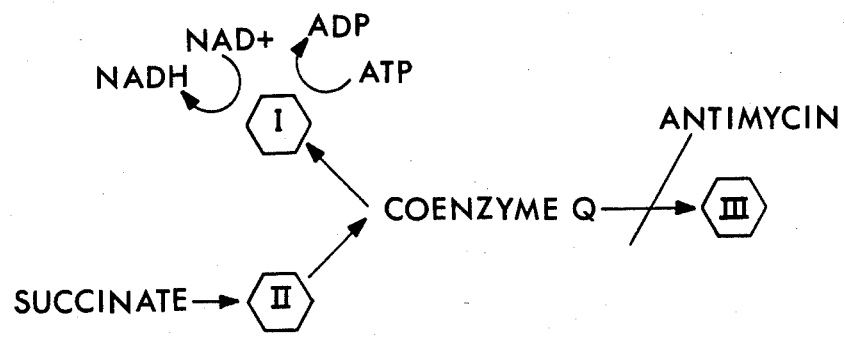
FIG. 2 illustrates the altered system created in the method of the preferred embodiment below.

In substance, the reverse electron transfer aspect of the present invention reverses the electron transfer which would normally occur from the enzyme complex I to coenzyme Q. This occurs by inhibiting the function of enzyme complex III by antimycin, and then making an excess of succinate for complex II enzymes. The effect of this is to drive an endergonic reduction of NAD+ to NADH as long as there is sufficient presence of ATP. For the process to be effective, therefore, there must be a sufficient quantity of NAD+ in the sample preparation to serve as a substrate for conversion by competent enzymes. It may also be required that other enzymes such as glutamate, or alcohol or pyruvate dehydrogenases be added from exogenous sources in the event these materials are lost by rupture of the intact mitochondria during particle preparation. This reverse electron transfer procedure is schematically illustrated in FIG. 2. As can be seen, if the enzymes and membranes of the mitochondrial preparations are competent, succinate will be consumed while NAD+ will be reduced to NADH as long as sufficient ATP is present. The process can be monitored spectrophotometrically to quantify the production of NADH.

In addition to the mitochondrial preparation, an assay medium is also necessary to perform the assay. The assay should contain suitable buffers and sugars, such as a TRIS-chloride buffer and sucrose, and should also contain the substrates and inhibitors necessary to drive the mitochondrial enzymes to or from a reaction product which can be measured. A magnesium salt may be appropriate to avoid sensitivity to calcium in the sample by the system. For a reverse electron transport assay in which NAD+ is to be reduced to NADH, one obvious requirement of the assay medium is NAD+ to be a substrate. To supply a source of electrons, succinate is a preferred substrate which can be oxidized by the complex II enzymes. In order to couple the donor electrons from succinate conversion to NAD+ reduction, it is necessary to block transport of the electron flow through complex III enzymes. This can be easily accomplished by adding antimycin, a known inhibitor of the complex III enzymes. With this combination, if the mitochondrial membranes and enzymes are otherwise functional, electrons would flow from coenzyme Q back through complex I enzymes to NAD+. Thus NAD+ would be reduced to NADH, as long as ATP was present to energize the conversion. Thus the initiation of the reaction can be controlled by the timing of ATP addition. While these particular substrates, inhibitor and energy source are preferred, other combinations are possible. For example, it is possible to derive energy for the reaction from coupling in the cytochrome oxidase complex by oxidation of ascorbate via the intermediate tetra-p-phenylenediamine in place of coupling in the ATPase complex with ATP. By varying the selection and combinations of buffers, substrates, energizers and enzyme inhibitors in the assay medium, the sensitivity of the test toward certain toxicants or types of toxicants (e.g. inhibitors of enzyme complex IV such as cyanide) can be greatly increased. Such variations in the assay medium offers the possibility of discriminating among different types of toxicants during analysis of environmental samples.

One advantage of this assay is that the reactants can be simply admixed in a common receptable, since the reaction can be controlled by withholding the energy source until desired. Normally, for convenience, the assay is run at 25° C., but any temperature between about 10° and 45° C. is suitable. As long as the reaction product, such as NADH, is to be assayed spectrophotometrically, the assay can most conveniently be performed in a spectrophotometer cuvette. Most cuvettes, such as the conventional 1 cm path length quartz cuvette, are usable in the present invention although it has been found that using a cuvette with 5 cm path length enables a lowering of protein concentration and an increase in sensitivity to many toxicants by as much as a factor of five times. Preferably the assay may be conducted by adding the mitochondrial preparation, the assay medium, and the assay sample to cuvette. A base line reading of optical adsorbancy can then be taken. The system can then be energized, as by addition of ATP, and adsorbancy re-measured after a standard time period, such as two minutes. To obtain a standard calibration curve and derive an effective response of 50%, successive tests at differing concentrations of toxicants must be performed so that dose-response can be calculated based on inhibition as plotted against the log of toxicant concentration. Longer preincubation times, i.e.

for 10 minutes, before adding the ATP or other energizing agent increases the sensitivity to some toxicants, as does increasing the reaction temperature.

To measure unknown concentrations of known or suspected pollutants in test samples, absorbance measured with the test sample is compared with the appropriate calibration curve. In the case of known toxicants this absorbance reading gives a quantitative analysis of the toxicant concentration in the sample. In the case of unknown toxicants, the shape of the dose-response curve obtained with various volumes of sample or separate chemical analysis can reveal the nature of the toxicant or toxicants of concern. However, the assay will generally be used simply to screen for general toxicity as a prelude to closer chemical or toxicological investigation by other qualitative methods. The assay can thus be efficiently used as a screening test to avoid repetitive testing on those samples which are free from toxicants so that monitoring programs can achieve savings and concentrate further testing on the samples of valid concern.

In general calibration curves can be used to determine the presence or absence of toxicants in water from a wide variety of suspect sources, e.g. industrial plant or municipal sewage treatment plant effluents, seepage from sanitary or secure landfills, or groundwater near pesticide storage and mixing areas. In areas known to be contaminated, to an unknown degree by a known toxicant, the calibration curves for that toxicant can be used to determine toxicant levels in all waste or wash streams associated with the toxicant.

EXAMPLE 1

A supply of submitochondrial particles were prepared by the method of Hansen and Smith, cited above, and frozen. Aliquots of the frozen submitochondrial particles with a protein concentration of 30 mg per ml were thawed and diluted with a cold solution of 0.25M sucrose in 10 mM TRIS-chloride buffer at pH 7.4 to give a final protein concentration of 6 mg per ml. This dilution created a working submitochondrial particle suspension which was stored on ice for a series of assays. An assay medium was prepared composed of 0.18M sucrose, 50 mM TRIS-chloride (pH 7.5), 6 mM magnesium sulfate, 1 mM NAD+, 5 mM potassium succinate and 0.2 µg per ml antimycin. To begin the assay, 2.9 ml of assay medium at 25° C. was placed in a 1-cm spectrophotometric cuvette. The toxicant was then added to the cuvette. The toxicant was added in solution in water, ethanol or dimethyl sulfoxide. The toxicant solution additions were in amounts of 20 µl or less in volumes and controls were also performed with pure solvent.

The assays were then commenced by adding 0.1 ml of the working submitochondrial particle suspension. The optical absorbance of the suspension at 340 nm was then monitored for two minutes to establish a base line. After two minutes, 50 µl of 0.2M K+ATP was added to energize the system. After two minutes the optical absorbance at 340 nm was again taken as a measure of the NAD+ reduction to NADH. To prepare calibration curves, successive tests were conducted using different concentrations of toxicant and the inhibition of NAD+ reduction observed. Dose-response curves were then determined from the test data by plotting percentage of inhibition versus the logarithm of toxicant concentration.

Results of these tests and calibrations are listed in Table 1 below. The results are compared to published results using the Microtox (TM) test and whole organism 96-hour fish tests.

TABLE I

| Toxicant Dose Response (parts per billion) for $EC_{50}$ | | | |
|---|---|---|---|
| Toxicant | Test Results | Microtox | Fish Test |
| Cadmium | 870 | 580,000 | 200 |
| Copper | 380 | 6,000 | 250 |
| Cyanide | 70 | 8,500 | 140 |
| 2,4-Dinitrophenol | 2,500 | 15,800 | — |
| Dinoseb (pesticide) | 50 | — | 67 |
| DNOC (pesticide) | 1,260 | 6,600 | 360 |
| Lead | 280 | 15,000 | 100 |
| Pentachlorophenol | 69 | 700 | 400 |
| Rotenone | 51 | — | 31 |
| Silver | 120 | — | — |
| Zinc | 1,600 | 26,000 | 2,200 |

EXAMPLE 2

A volume of 2.9 ml of water sample containing an unknown concentration of pentachlorophenol was added to a cuvette containing an aliquot of the assay medium as in Example 1 above and equilibrated at 25° C. After addition of 0.1 ml of the working suspension of submitochondrial particles, equilibration for two minutes, and addition of ATP, the absorbance at 340 nm was measured after two more minutes and recorded. By reference to a calibration curve, the reading indicated an EC of 39%, i.e. an inhibition of 39% of the maximum NADH concentration, and a penta chlorophenol concentration in water of 16 ppb.

EXAMPLE 3

A 2.9 ml aliquot of herbicide application equipment wash water containing an unknown concentration of 2-methyl-4, 6-dinitrophenol (dinitro-o-cresol or DNOC) was added to assay medium and a suspension of submitochondrial particles as in Example 1 above, and assayed. Reference to a calibration curve indicated an EC of 20% and hence a concentration of 200 ppb. A second washing, similarly assayed showed an EC of 13% and a concentration of 133 ppb.

We claim:

1. A method of assaying for toxicants in an environmental sample comprising the steps of:
   combining in a common receptacle (a) a suspension of submitochondrial particles formed from the inner membranes of mitochondria and carrying competent mitochondrial enzymes thereon, (b) an assay medium includng a substrate, the conversion of which by mitochondrial enzymes can be detected by spectrophotometric detection of one of the substrate and its enzymatic reaction product, and (c) a quantity of the environmental sample to be tested; and
   measuring spectrophotometrically the conversion of the substrate to determine the effect of the sample on the activity of the enzymes in the suspension particles.

2. An assay method as claimed in claim 1 wherein the submitochondrial particles are prepared by sonicating whole mitochondria and allowing the cristae membranes to reform into micelles.

3. An assay method as claimed in claim 1, further comprising the step, before the combining in a common receptacle, of thawing the submitochondrial particles which have been previously prepared and then frozen or freeze-dried for stable storage.

4. An assay method as claimed in claim 1 wherein the substrate is NAD+, which is reduced enzymatically to NADH, the presence of which can be detected spectrophotometrically at 340nm.

5. An assay method as claimed in claim 1 wherein the assay medium also includes a buffer salt.

6. An assay method as claimed in claim 1 wherein the assay medium also includes an electron source to supply electrons that flow through the mitochondrial enzymes to cause conversion of the substrate.

7. An assay method as claimed in claim 6 wherein the electron source is a succinate ion.

8. An assay method as claimed in claim 6 wherein the assay medium also includes an enzyme inhibitor to cause the elecltrons to flow toward the enzymes which act on the substrate.

9. An assay method as claimed in claim 8 wherein the enzyme inhibitor is antimycin.

10. An assay method as claimed in claim 1 wherein the assay medium also includes magnesium ion to reduce calcium disruption of the mitochondrial enzymes.

11. An assay method as claimed in claim 1 further comprising the step, before the measuring step, of adding a quantity of an energy source to the suspension effective to selectively energize the conversion reaction.

12. An assay method as claimed in claim 11 wherein the energy source is ATP.

13. An assay method as claimed in claim 11 further comprising the step, before adding the energy source, of pre-measuring the spectrophotometric response of the suspension to establish a baseline value.

14. An assay method as claimed in claim 1 further comprising the step of repeating the assay with different concentrations or volumes of the sample and plotting the dose-response curve of the sample to determine relative toxicity of different concentrations or volumes of the sample.

15. An assay method as claimed in claim 1 wherein the suspension, the assay medium and the sample are added thereto are mixed in a spectrophotometric cuvette.

16. A method of assaying for the presence of toxicants in a sample by spectrophotometric analysis comprising the steps of
preparing a suspension including at least portions of mitochondrial membranes having competent oxidative phophorylation enzyme complexes I and II and ATPase thereon;
adding the suspension to an assay medium including buffer salts; a magnesium ion, NAD+; succinate ion and antimycin, so that the conversion of succinate by complex II enzyme will cause reverse electron flow to cause reduction of NAFD+ to NADH by complex I enzymes if an energy source is present;
adding a quantity of the sample;
measuring the base-line spectrophotometric response of the suspension at 340 nm to determine base-line NADH concentration;
adding a quantity of an energy source to the suspension; and
measuring the spectorphotometric response of the suspension at 340 nm to determine the increase of NADH concentration, which increase is affected by the presence of any toxicants in the sample.

17. An assay method as claimed in claim 16 wherein the mitochondrial membrane suspension was previously frozen freeze-dried and stored for use in the assay.

18. An assay method as claimed in claim 16 wherein the assay medium further includes a magnesium ion to reduce calcium disruption of the mitochondrial enzymes.

19. An assay method as claimed in claim 16 wherein the energy source is ATP.

20. An assay method as claimed in claim 16 further comprising the step of repeating the assay with varying concentrations of the sample and plotting the dose-response curve of the sample to determine the relative toxicity of the sample.

21. A kit for use in spectrophotometrically assaying for toxicants in an environmental sample comprising
a suspension of submitochondrial particles carrying competent enzymes thereon;
an assay medium comprising a buffer salt; a reaction substrate, the covnersion of which by a mitochondrial enzyme can be detected spectrophotoemtrically; an electron source; and a selective metochondrial enzyme inhibitor, all selected so that the electron source casues enzymatic conversion of the reaction substrate in the non-inhibited competent mitochondrial enzymes upon the addition of an energy source; and
an energy source to drive the conversion of the reaction substrate so that the enzymatic conversion reaction can be monitored spectrophotometrically.

22. A kit as claimed in claim 21 wherein the submitochondrial particles are freeze-dried.

23. A kit as claimed in claim 21 wherein the reaction substrate is NAD+ which can be reduced by enzyme complex I on the submitochondrial particles to NADH, which can be detected spectrophotometrically at 340 nm.

24. A kit as claimed in claim 21 wherein the electron source is succinate.

25. A kit as claimed in claim 21 wherein the enzyme inhibitor is antimycin.

26. A kit as claimed in claim 21 wherein the energy source is ATP.

27. A kit as claimed in claim 21 wherein the assay medium also includes magnesium ion to prevent calcium disruption of the mitochondrial enzymes.

* * * * *